(12) United States Patent
Anderson

(10) Patent No.: US 11,154,388 B2
(45) Date of Patent: Oct. 26, 2021

(54) SURGICAL INSTRUMENTS AND METHODS OF USE

(71) Applicant: Michael John Anderson, Beverly Shores, IN (US)

(72) Inventor: Michael John Anderson, Beverly Shores, IN (US)

( * ) Notice: Subject to any disclaimer, the term of this patent is extended or adjusted under 35 U.S.C. 154(b) by 90 days.

(21) Appl. No.: 16/050,456

(22) Filed: Jul. 31, 2018

(65) Prior Publication Data

US 2020/0038162 A1 Feb. 6, 2020

(51) Int. Cl.
*A61D 1/08* (2006.01)

(52) U.S. Cl.
CPC ...................... *A61D 1/08* (2013.01)

(58) Field of Classification Search
CPC ..... A61B 17/285; A61B 16/28; A61B 17/062; A61B 17/3201; A61B 2017/2837; A61B 2017/00353; A61D 1/08
See application file for complete search history.

(56) References Cited

U.S. PATENT DOCUMENTS

| | | | | |
|---|---|---|---|---|
| 2,323,183 | A * | 6/1943 | Alleyne | A61B 17/28 606/119 |
| 4,827,929 | A * | 5/1989 | Hodge | A61B 17/062 606/139 |
| 5,176,701 | A | 1/1993 | Dusek et al. | |
| 6,001,120 | A * | 12/1999 | Levin | A61B 17/282 606/174 |
| 6,976,992 | B2 | 12/2005 | Sachatello et al. | |
| 7,722,639 | B2 | 5/2010 | Dowling | |
| D669,987 | S | 10/2012 | Bashir | |
| 2008/0172085 | A1 * | 7/2008 | Chiu | A61B 17/282 606/205 |
| 2015/0157350 | A1 | 6/2015 | Graham | |
| 2016/0235425 | A1 | 8/2016 | Ohki | |
| 2016/0235498 | A1 * | 8/2016 | Stanley | A61B 17/285 |
| 2017/0056038 | A1 * | 3/2017 | Hess | A61B 17/29 |
| 2018/0168568 | A1 * | 6/2018 | Ali | A61B 17/285 |

FOREIGN PATENT DOCUMENTS

| | | |
|---|---|---|
| JP | 10165426 | 6/1998 |
| KR | 20100086155 | 7/2010 |

OTHER PUBLICATIONS

International Search Report for International Patent Application No. PCT/US2019/039502, dated Oct. 18, 2019, (3 pages).

* cited by examiner

*Primary Examiner* — Darwin P Erezo
*Assistant Examiner* — Raihan R Khandker
(74) *Attorney, Agent, or Firm* — Hartman Global IP Law; Gary M. Hartman; Domenica N. S. Hartman

(57) ABSTRACT

Surgical instruments suitable for use during surgical procedures. The surgical instruments include first and second halves coupled together at a pivot so that the halves define a handle and functional portions at proximal and distal ends of the instrument, respectively. The functional portion terminates at a blunt distal end and includes scissors, a base section disposed between the scissors and blunt distal end and having a first clamping feature, a tapering section disposed between the first clamping feature and blunt distal end and having gripping features, and opposing tips disposed between the tapering section and distal end of the instrument and having second clamping features.

10 Claims, 6 Drawing Sheets

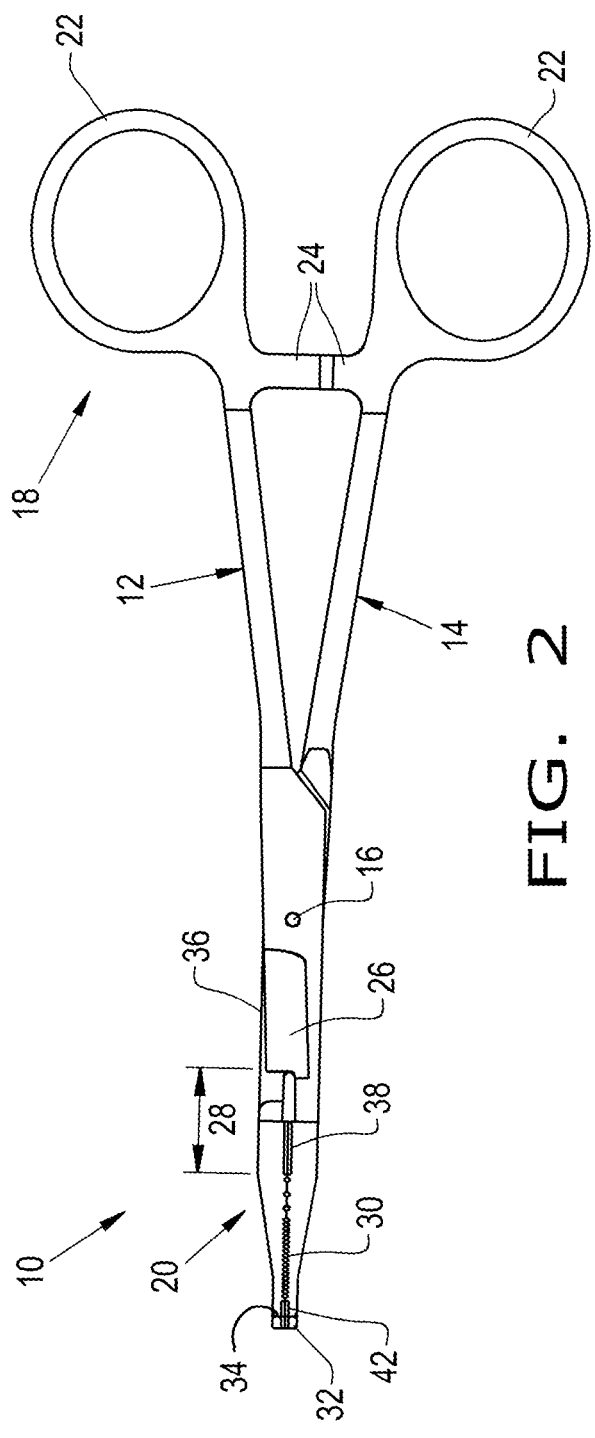
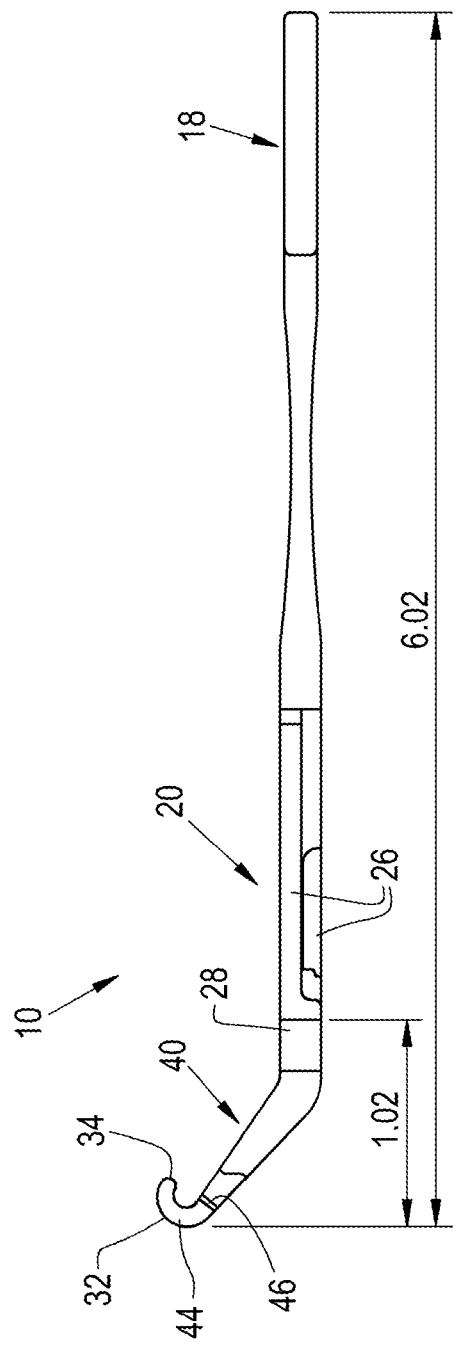
FIG. 2
FIG. 3

SURGICAL INSTRUMENTS AND METHODS OF USE

BACKGROUND OF THE INVENTION

The present invention generally relates to surgical instruments and methods for their use during surgical procedures.

Surgical instruments for performing ovariohysterectomies (spaying) on domesticated female animals, including but not limited to dogs and cats, are often available in a surgery pack that contains multiple instruments for performing the various different steps during the procedure, for example, to exteriorize the ovaries and uterine horns, ligate the ovarian arteries, and then transect the ovarian arteries. The sheer number of instruments, for example, nineteen in some general surgery packs that are commercially available, can result in the surgeon having to sort through multiple instruments to find a particular instrument required for a given step of the procedure. Prior to surgery the instruments can be separated and organized according to their particular uses and features in an effort to reduce time loss. However, all of the instruments must be processed postoperatively, for example, cleaning, separating, packing, sterilizing, etc., regardless of which instruments are used. Finally, surgical instruments for performing ovariohysterectomies often have redundancies in form and function.

Therefore, there is a desire to reduce the number of surgical instruments required to perform ovariohysterectomies and other surgical procedures.

BRIEF DESCRIPTION OF THE INVENTION

The present invention provides surgical instruments suitable for use during surgical procedures, for example, an ovariohysterectomy. The surgical instruments are equipped with features capable of providing multiple functionalities, including but not limited to cutting, clamping, gripping, retracting, and/or capturing suture threads, tissue, and internal organs during a surgical procedure.

According to one aspect of the invention, such a surgical instrument includes first and second halves coupled together at a pivot so that the first and second halves define a handle portion at a proximal end of the instrument and a functional portion at a distal end of the instrument with the pivot therebetween. The functional portion terminates at a blunt distal end. Scissors are disposed in the functional portion adjacent to the pivot and are defined by complementary scissor features of the first and second halves. A base section is disposed in the functional portion between the scissors and the blunt distal end of the functional portion, and the base section comprises first clamping means defined by complementary first clamping features of the first and second halves. A tapering section is disposed in the functional portion between the first clamping means and the blunt distal end of the functional portion. The tapering section comprises gripping means defined by opposing serrated features on each of the first and second halves. Opposing tips are defined by the first and second halves and disposed in the functional portion between the tapering section and the distal end of the instrument. The tips define the blunt distal end of the functional end and comprise second clamping means defined by complementary second clamping features of the first and second halves.

Other aspects of the invention include surgical procedures that use a surgical instrument of a type described above. A particular but nonlimiting example is an ovariohysterectomy.

Technical aspects of the instruments and procedures described above preferably include the ability of the instruments to have multiple functionalities, for example, to function as a needle holder, clamp, tissue grasping forceps, retractor, and/or surgical scissors.

Other aspects and advantages of this invention will be appreciated from the following detailed description.

BRIEF DESCRIPTION OF THE DRAWINGS

FIGS. 1, 2, and 3 are perspective, plan, and side views of a surgical instrument in accordance with a nonlimiting embodiment of this invention.

DETAILED DESCRIPTION OF THE INVENTION

Figure 1:
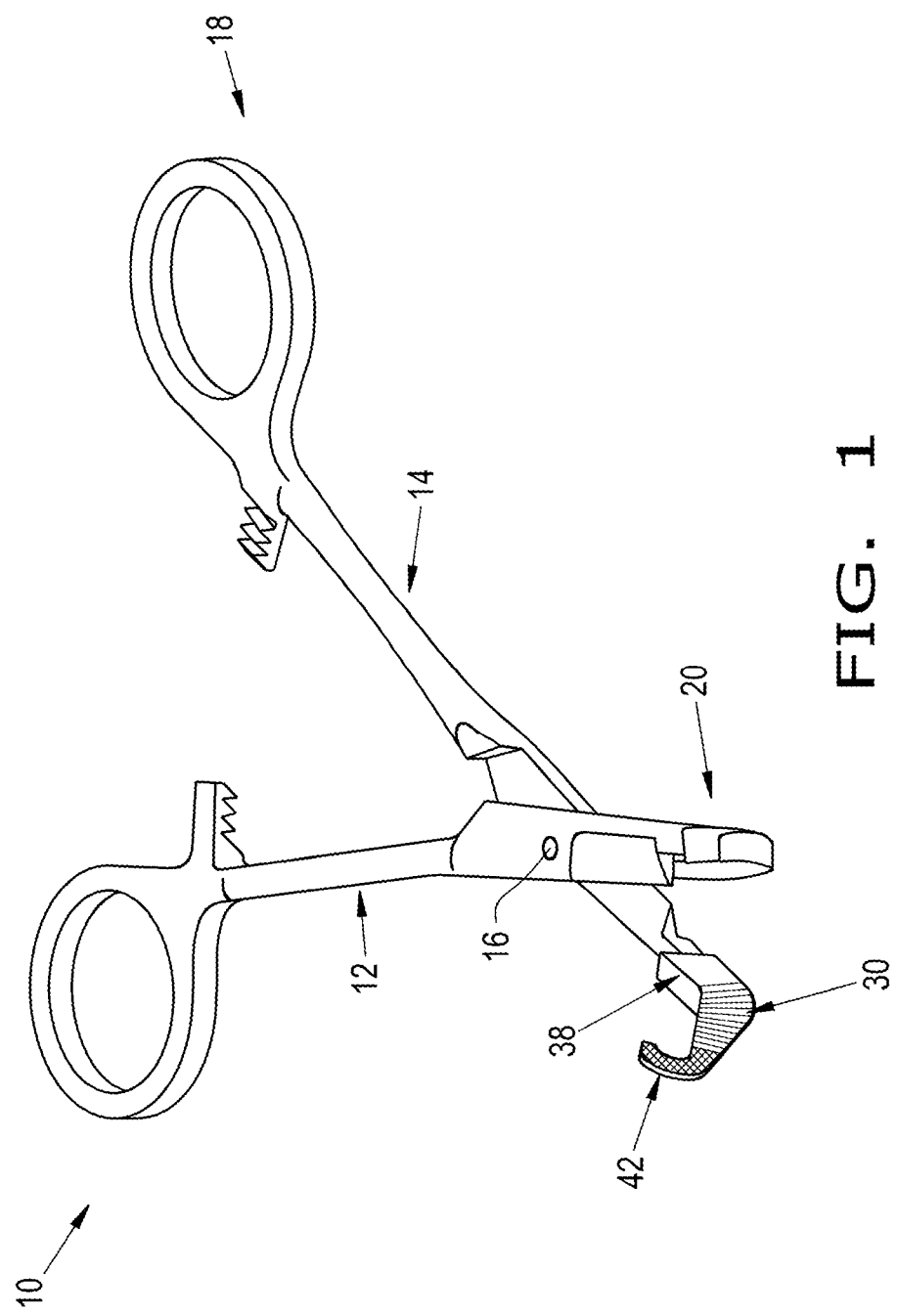
Figure 4:
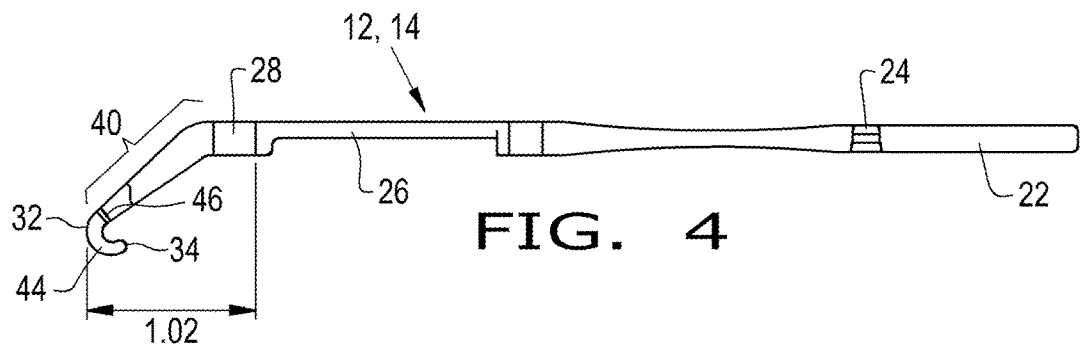
FIGS. 4, 5, and 6 are various views of one-half of the surgical instrument of FIGS. 1, 2, and 3.
Figure 5:
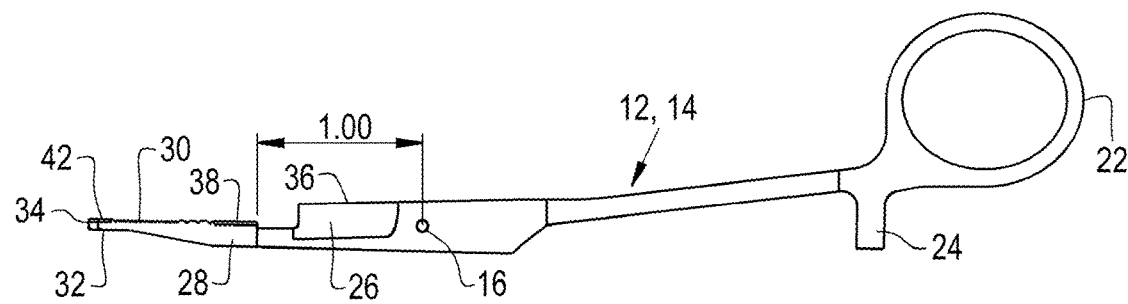
Figure 6:
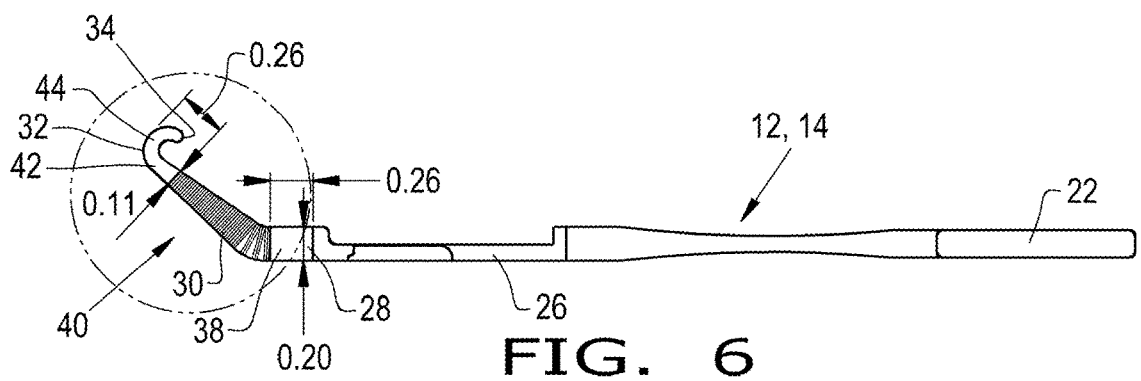
Figure 7:
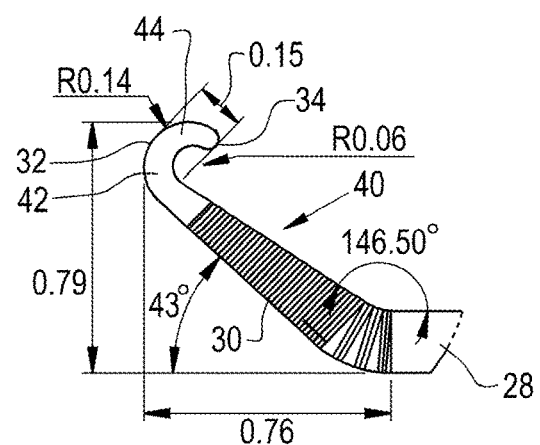
FIG. 7 is a detail taken from FIG. 6.
Figure 8:
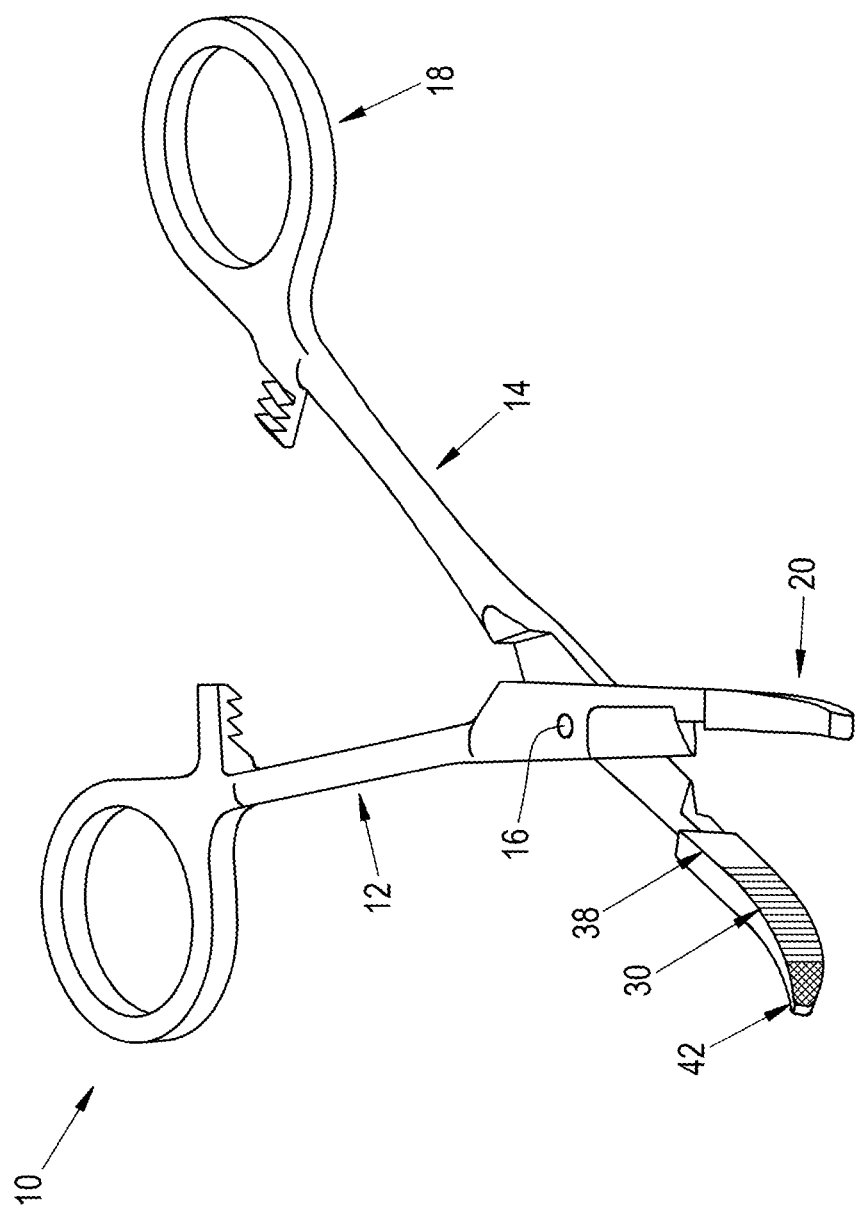
FIGS. 8, 9, and 10 are perspective, plan, and side views of a surgical instrument in accordance with another nonlimiting embodiment of this invention.
Figure 9:
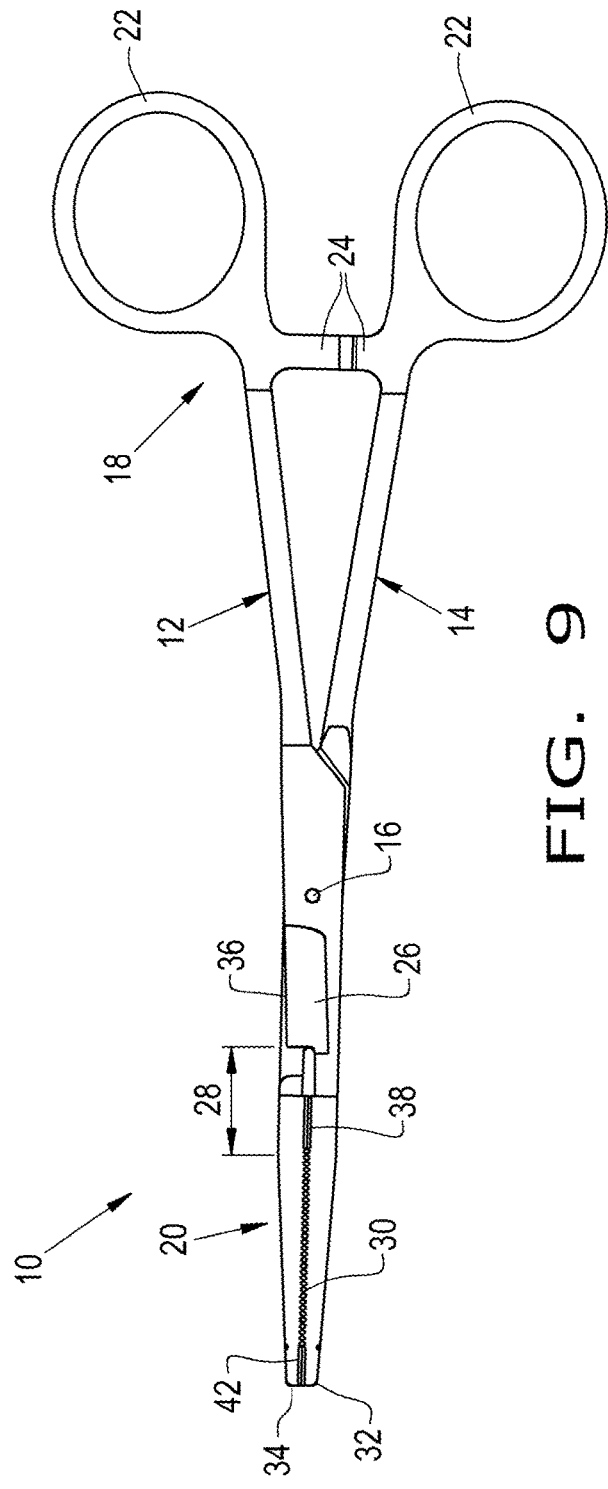
Figure 10:
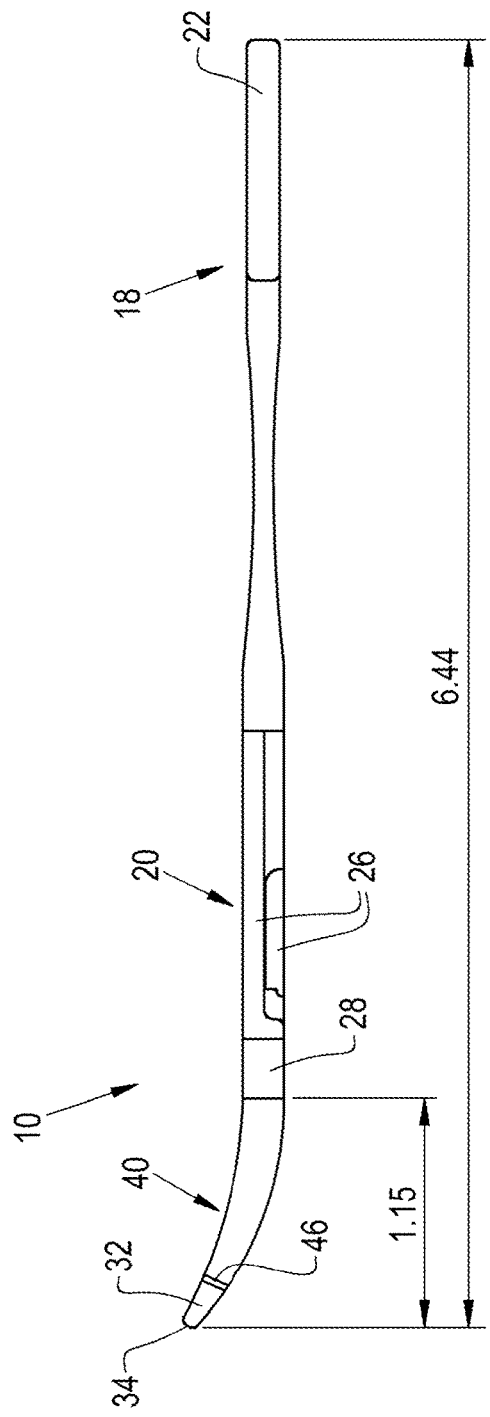
Figure 11:
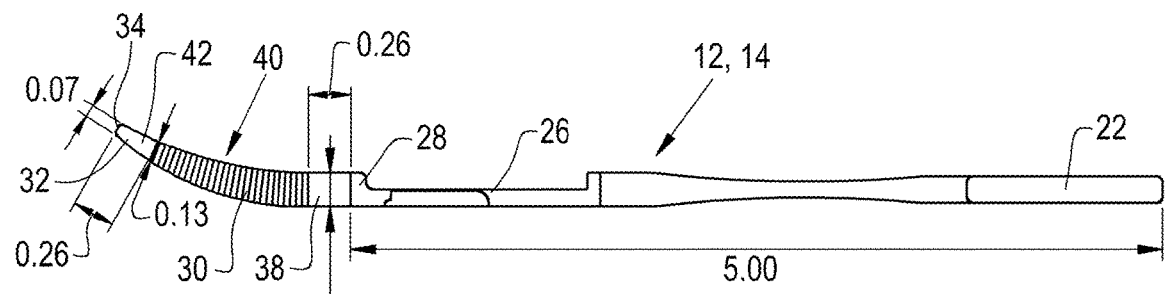
FIGS. 11, 12, and 13 are various views of one-half of the surgical instrument of FIGS. 8, 9, and 10.
Figure 12:
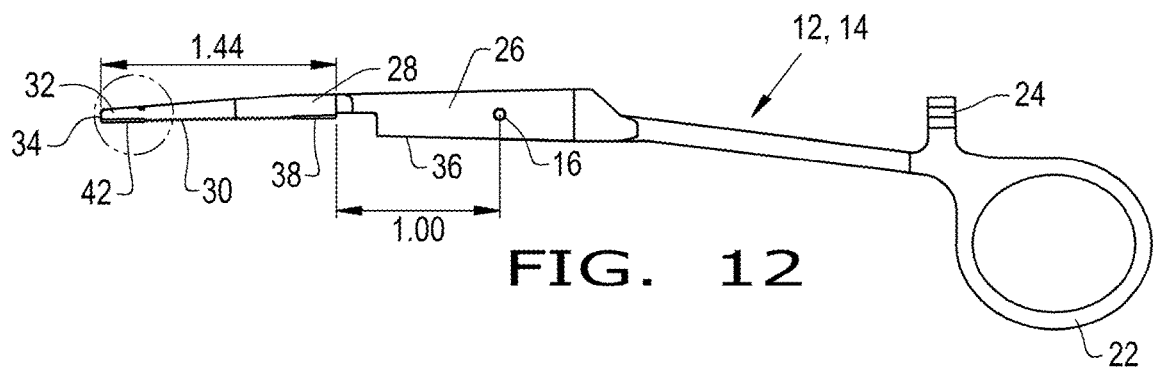
Figure 13:
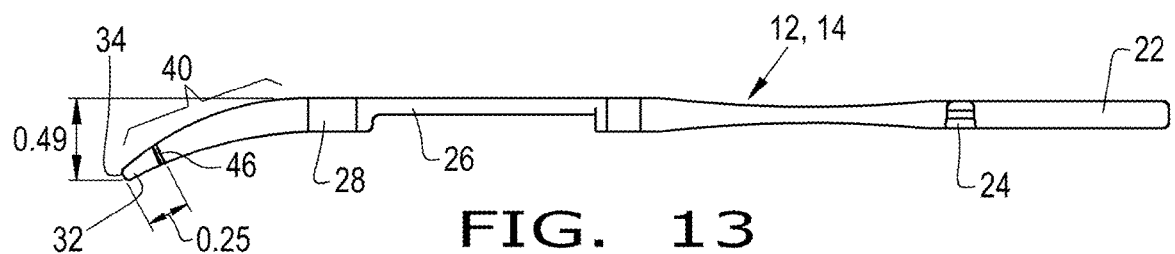
Figure 14:
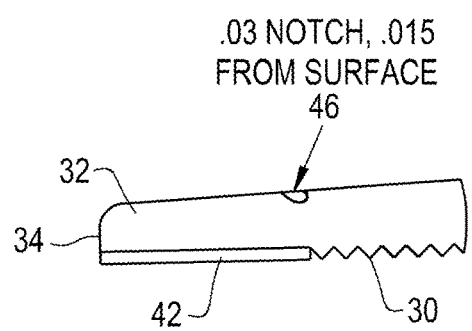
FIG. 14 is a detail taken from FIG. 12.

FIGS. 1 through 14 represent various views of two nonlimiting embodiments of surgical instruments that are within the scope of the present invention. Although the invention will be described hereinafter in reference to the surgical instruments adapted for use in an ovariohysterectomy procedure, it will be appreciated that the teachings of the invention are more generally applicable to surgical instruments that can be employed during a variety of surgical procedures.

To facilitate the description provided below of the embodiments represented in the drawings, relative terms may be used in reference to the orientations of the instruments as represented in some of the drawings. All such relative terms are intended to indicate the construction and relative orientations of components and features of the instruments, and therefore are relative terms that are useful to describe the illustrated embodiments but should not be otherwise interpreted as limiting the scope of the invention. The drawings disclose certain dimensions for the instruments that are believed to be preferred or exemplary, but are otherwise not necessarily limitations to the scope of the invention.

FIGS. 1 through 7 represent a surgical instrument 10 with certain general features similar to an Olsen-Hegar needle holder. The instrument 10 comprises two halves 12 and 14 that are substantially mirror images of each other. The halves 12 and 14 may be pivotably connected at a pivot 16 in a conventional manner. In FIGS. 2 through 6, portions of the halves 12 and 14 to the right of the pivot 16 (referred to herein as the proximal end of the instrument 10) generally define the handle 18 of the instrument 10, and portions of the halves 12 and 14 to the left of the pivot 16 (referred to herein as the distal end of the instrument 10) generally define what will be referred to herein as the functional end 20 of the instrument 10. The "handle" portions of the halves 12 and 14 defining the handle 18 include finger loops 22 and complementary interlocking members 24 that may also be configured and operate in a generally conventional manner.

The "functional" portions of the halves 12 and 14 that define the functional end 20 of the instrument 10 comprise complementary scissor features 26 that define scissors in close proximity to the pivot 16. Progressing in the distal direction of the instrument 10, the functional end 20 further comprises complementary base sections 28, opposing serrated features 30, and opposing tips 32. Each tip 32 defines a blunt distal end 34 of its corresponding functional end 20. The scissor features 26 have lateral widths (i.e., in the plane of each half 12 and 14 as viewed in FIG. 5) that is substantially the same as the lateral width of the half 12 and 14 at the pivot 16 to allow a wider opening of the instrument 10 prior to scissor edges 36 of the scissor features 26 being exposed. The base sections 28 are each equipped with an insert 38 formed of a relatively harder material, for example, tungsten carbide (WC). The inserts 38 oppose each other so as to provide clamping means. As a particular example, the inserts 38 are adapted to provide a needle holder function with the capability of a greater driving force of a suture needle since the inserts 38 are longitudinally aligned with the overall design of the instrument 10 (e.g., see FIG. 6). As a result, there is less tendency for a side to side motion of a needle when clamped between the inserts 38 because their location is more proximal to the pivot 16 of the instrument 10 than the remainder of the functional end 20 located closer to the blunt distal end 34.

In the distal direction of the instrument 10, the serrated features 30 and tips 32 gradually taper toward the blunt distal end 34 to define what is referred to herein as straight tapering section 40. The straight tapering section 40 can be seen in FIGS. 3, 4, 6, and 7 as being oriented at a substantially constant obtuse angle to the proximal part of the functional end 20 in which the scissor features 26 and base section 28 are defined. The serrated features 30 of the halves 12 and 14 oppose each other to provide a gripping means on the functional end 20 of the instrument 10. The obtuse angle and straightness of the tapering section 40 are adapted to contribute an ergonomic function to the overall shape of the instrument 10 of FIGS. 1 through 7. As an example, features located within and distal of the straight tapering section 40 (e.g., 32, 34, 42, 44, and 46 discussed below) can be more easily used as a needle holder, tissue grasping forceps, and retractor, and to capture of arteries/veins. The serrated features 30 are particularly well suited for clamping hollow tubular organs, including blood vessels.

The tips 32 of the halves 12 and 14 are equipped with opposing inserts 42, each formed of a relatively harder material, for example, tungsten carbide (WC), to provide a second clamping means on the functional end 20 of the instrument 10 As a particular example, the inserts 42 are adapted to provide a needle holder function for driving and catching a needle through tissue. In addition, the inserts 42 can be utilized for grasping tissue as a forceps when passing a needle through tissue during suturing, and also utilized to capture a suture for knot tying.

Each tip 32 terminates with a hook 44 that defines the blunt distal end 34 of its half 12 or 14. Each hook 44 is shown as defining an arc that approaches but is less than 180 degrees, which is believed to promote the ability of the hooks 44 (individually or together) to be utilized for retraction of anatomical structures and capturing internal organs as well as knot tying of arteries/veins back onto themselves. Complementary notches 46 can be defined in the opposite surfaces of the tips 32 and utilized to catch suture and/or arteries/veins sliding down the outside of the instrument 10 from proximal to distal.

The instrument represented in FIGS. 8 through 14 is generally similar in general construction to the instrument 10 of FIGS. 1 through 7. For convenience, identical reference numerals are used in FIGS. 8 through 14 to denote the same or functionally related or equivalent elements that were described for the instrument 10 of FIGS. 1 through 7. In view of similarities between the embodiments of FIGS. 1 through 7 and FIGS. 8 through 14, the following discussion of the instrument 10 of FIGS. 8 through 14 will focus primarily on aspects of the second embodiment that differ from the first embodiment in some notable or significant manner. Other aspects of the second embodiment not discussed in any detail can be, in terms of structure, function, materials, etc., essentially as was described for the first embodiment.

In the distal direction of the instrument 10 of FIGS. 8 through 14, the serrated features 30 and tips 32 gradually taper toward the blunt distal end 34 to define what is referred to herein as curved tapering section 40. The curved tapering section 40 can be seen in FIGS. 3, 4, 6, and 7 as being substantially continuously curved starting at the proximal part of the functional end 20 in which the scissor features 26 and base section 28 are defined, and continuing to the blunt distal end 34 of each half 12 and 14. Each tip 32 terminates without the hook 44 described for the embodiment of FIGS. 1 through 7, but instead is relatively straight or a continuation of the curvature of the tapering section 40. Similar to the straight tapering section 40 of FIGS. 1 through 7, the curvature of the curved tapering section 40 is adapted to contribute an ergonomic function to the overall shape of the instrument 10, so that the features located within and distal of the curved tapering section 40 (e.g., 32, 34, 42, 44, and 46) can be more easily used as a needle holder, tissue grasping forceps, and retractor, and to capture of arteries/veins.

During a surgical procedure, the tips 32 and their inserts 42 are functional as needle holders and tissue grasping forceps, the base sections 28 and their inserts 38 are functional as needle holders, the serrated features 30 are functional as tissue clamps, the hooks 44 are functional as retractors and to capture veins and arteries, the notches 46 are functional to capture veins and arteries, and the scissor features 26 are functional as surgical scissors for cutting sutures and tissue. The straight tapering section 40 of FIGS. 1 through 7 and the curved tapering section 40 of FIGS. 8 through 14 promote the ability of their respective instruments 10 to grasp tissue at their blunt distal ends 34 while also achieving a high range of visibility.

While the invention has been described in terms of particular embodiments, it should be apparent that alternatives could be adopted by one skilled in the art. For example, the instruments 10 and their components could differ in appearance and construction from the embodiments described herein and shown in the drawings, functions of certain components of the instruments 10 could be performed by components of different construction but capable of a similar (though not necessarily equivalent) function, and various materials could be used in the fabrication of the instruments 10 and/or their components. As such, it should be understood that the above detailed description is intended to describe the particular embodiments represented in the drawings and certain but not necessarily all features and aspects thereof, and to identify certain but not necessarily all alternatives to the embodiments and described features and aspects. As a nonlimiting example, the invention encompasses additional or alternative embodiments in which one or more features or aspects of a particular embodiment could be eliminated or two or more features or aspects of different embodiments could be combined. Accordingly, it should be understood that the invention is not necessarily limited to any embodiment described herein or illustrated in the drawings, and the phraseology and terminology employed above are for the purpose of describing the illustrated embodiments and do not necessarily serve as limitations to the scope of the invention. Therefore, the scope of the invention is to be limited only by the following claims.

The invention claimed is:

1. A surgical instrument comprising:
   first and second halves coupled together at a pivot so that the first and second halves each define a handle portion at a proximal end of the instrument and a functional portion at a distal end of the instrument with the pivot therebetween, the functional portions of the first and second halves together defining a functional end of the instrument that terminates at a blunt distal end of each of the first and second halves;
   scissors disposed in the functional end adjacent the pivot and defined by complementary scissor features of the first and second halves;
   a base section disposed in the functional end between the scissors and the blunt distal ends of the first and second halves, the base section comprising first clamping means defined by complementary first clamping features of the first and second halves;
   a tapering section disposed in the functional end between the first clamping means and the blunt distal ends of the first and second halves, the tapering section comprising gripping means defined by opposing serrated features on each of the first and second halves;
   opposing first and second tips defined respectively by the first and second halves and disposed in the functional end between the tapering section and the blunt distal ends of the first and second halves, the first and second tips comprising second clamping means defined by complementary second clamping features of the first and second halves; and
   a single hook means within the functional end and defined by the first and second tips terminating with first and second hooks, respectively, that define the blunt distal ends of the first and second halves, respectively, each of the first and second hooks defining an opposing half of the blunt distal ends of the first and second halves, the first and second hooks being mirror images of each other so that the first and second hooks together define the single hook means and the single hook means defines an arc of greater than 90 degrees but is less than 180 degrees for retraction of anatomical structures and capturing internal organs.

2. The surgical instrument of claim 1, wherein the first and second halves comprise complementary means for interlocking the handle portion.

3. The surgical instrument of claim 1, wherein the tapering section is straight and disposed at a substantially constant obtuse angle to the base section.

4. The surgical instrument of claim 1, wherein the tapering section is curved relative to the base section.

5. The surgical instrument of claim 1, wherein the scissor features have lateral widths that are each substantially equal to lateral widths of each of the first and second halves at the pivot.

6. The surgical instrument of claim 1, wherein the complementary first clamping features are tungsten carbide inserts.

7. The surgical instrument of claim 1, wherein the complementary second clamping features are tungsten carbide inserts.

8. The surgical instrument of claim 1, wherein the first and second halves have opposite outside surfaces that are disposed on outside surfaces of the surgical instrument, the surgical instrument further comprising complementary notches defined in the opposite outside surfaces of the first and second halves at the first and second tips so that the complementary notches face away from each other, the notches defining means for catching sutures, arteries, and veins sliding down the outside surfaces of the surgical instrument.

9. A surgical procedure comprising use of the surgical instrument of claim 1, the surgical procedure comprising:
   using the first and second tips and the second clamping features thereof as a needle holder;
   using the base sections and the first clamping features thereof as a clamp;
   using the serrated features as tissue clamps; and
   using the scissor as surgical scissors.

10. A surgical procedure comprising use of the surgical instrument of claim 1, the surgical procedure comprising: wherein the surgical instrument further comprises complementary notches defined in opposite surfaces of the first and second tips so that the complementary notches face away from each other, and the surgical procedure comprises using the notches to capture arteries and/or veins.

* * * * *